(12) United States Patent
Presura (10) Patent No.: US 11,134,854 B2
(45) Date of Patent: Oct. 5, 2021

(54) PHYSIOLOGICAL PROPERTY DETERMINATION APPARATUS

(71) Applicant: KONINKLIJKE PHILIPS N.V., Eindhoven (NL)

(72) Inventor: Cristian Nicolae Presura, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1022 days.

(21) Appl. No.: 15/116,116

(22) PCT Filed: Feb. 13, 2015

(86) PCT No.: PCT/EP2015/053037
§ 371 (c)(1),
(2) Date: Aug. 2, 2016

(87) PCT Pub. No.: WO2015/132063
PCT Pub. Date: Sep. 11, 2015

(65) Prior Publication Data
US 2017/0172435 A1      Jun. 22, 2017

(30) Foreign Application Priority Data

Mar. 6, 2014 (EP) ..................................... 14158128

(51) Int. Cl.
*A61B 5/024* (2006.01)
*A61B 5/00* (2006.01)

(52) U.S. Cl.
CPC ...... *A61B 5/02427* (2013.01); *A61B 5/02416* (2013.01); *A61B 5/02438* (2013.01); *A61B 5/681* (2013.01); *A61B 5/721* (2013.01)

(58) Field of Classification Search
None
See application file for complete search history.

(56) References Cited

U.S. PATENT DOCUMENTS

2007/0123787 A1      5/2007   Kitajima et al.
2007/0299330 A1*    12/2007   Couronne .......... A61B 5/02416
                                                                    600/368

(Continued)

FOREIGN PATENT DOCUMENTS

CN       202981974 A       6/2013
JP       2008301934 A     12/2008

(Continued)

OTHER PUBLICATIONS

Hyvärinen et al., "Principal component analysis". Natural Image Statistics, pp. 1-11, Mar. 2009. (Year: 2009).*

(Continued)

*Primary Examiner* — Yi-Shan Yang (57) ABSTRACT

The invention relates to a physiological property determination apparatus (1) for determining a physiological property like a pulse rate of a person. The apparatus may be configured to be worn on the wrist like a watch. A controller (8) separately controls at least two light sources (3, 4, 5) for emitting at least two light beams having different wavelengths into tissue of the person and a light detector (6) having a two-dimensional detection surface (12) detects light, which has travelled through the tissue, wavelength-dependently and generates a wavelength-dependent two-dimensional image based on the detected light. Based on the generated wavelength-dependent two-dimensional image the physiological property is determined. The separate control of the light sources allows for an independent optimization of the illumination and detection processes for each wavelength, which in turn can lead to an improved determination of the physiological property based on the wavelength-dependent two-dimensional image.

15 Claims, 4 Drawing Sheets

(56) References Cited

U.S. PATENT DOCUMENTS

| | | |
|---|---|---|
| 2009/0018408 A1 | 1/2009 | Ouchi et al. |
| 2009/0306487 A1* | 12/2009 | Crowe ............... A61B 5/02433 |
| | | 600/322 |
| 2010/0090798 A1* | 4/2010 | Garcia Molina .... G06K 9/0055 |
| | | 340/5.53 |
| 2010/0217098 A1* | 8/2010 | LeBoeuf ............. A61B 5/7221 |
| | | 600/301 |
| 2010/0268094 A1 | 10/2010 | Hasling et al. |
| 2012/0141000 A1 | 6/2012 | Jeanne et al. |
| 2012/0195486 A1 | 8/2012 | Kirenko et al. |
| 2013/0030307 A1 | 1/2013 | Rajan et al. |
| 2013/0131475 A1* | 5/2013 | Eisen ................ A61B 5/14552 |
| | | 600/324 |
| 2013/0204112 A1* | 8/2013 | White ................. A61B 5/0261 |
| | | 600/407 |
| 2013/0265401 A1* | 10/2013 | Igarashi .............. A61B 1/0661 |
| | | 348/68 |
| 2014/0323888 A1* | 10/2014 | Kyal ................... A61B 5/02405 |
| | | 600/508 |
| 2015/0006114 A1* | 1/2015 | Altbach ................. A61B 5/055 |
| | | 702/189 |
| 2015/0065896 A1 | 3/2015 | Takahashi |
| 2016/0015308 A1* | 1/2016 | Kirenko .................. A61B 5/222 |
| | | 600/301 |
| 2017/0319114 A1* | 11/2017 | Kaestle ................ A61B 5/0077 |

FOREIGN PATENT DOCUMENTS

| | | |
|---|---|---|
| JP | 2010137110 A | 6/2010 |
| SU | 888931 A1 | 12/1981 |
| WO | 2009100776 A1 | 8/2009 |
| WO | 2009111446 A1 | 9/2009 |
| WO | 2011026986 A1 | 3/2011 |
| WO | WO-2013017976 A1 * | 2/2013 ........... A61B 5/0077 |
| WO | 2013030744 A1 | 3/2013 |

OTHER PUBLICATIONS

Ricketts et al., "Non-invasive blood perfusion measurements using a combined temperature and heat flux surface probe". Int J Heat Mass Transf. 2008; 51(23-24): 5740-5748. (Year: 2008).*

* cited by examiner

PHYSIOLOGICAL PROPERTY DETERMINATION APPARATUS

CROSS-REFERENCE TO PRIOR APPLICATIONS

This application is the U.S. National Phase application under 35 U.S.C. § 371 of International Application No. PCT/EP2015/053037, filed on Feb. 13, 2015, which claims the benefit of European Patent Application No. 14158128.0 filed on Mar. 6, 2014. These applications are hereby incorporated by reference herein, for all purposes.

FIELD OF THE INVENTION

The invention relates to a physiological property determination apparatus, method and computer program for determining a physiological property of a person.

BACKGROUND OF THE INVENTION

US 2010/0268094 A1 discloses an apparatus for determining a pulse rate of a person. The apparatus comprises a light source for emitting light into a body part and a digital camera to be placed near or in contact with the body part, in order to detect the light after having traversed the body part, wherein the pulse rate is determined based on variations of the detected light. However, depending on the light source used for illuminating the body part, the camera and the kind of body, through which the light travels, the accuracy of the determined pulse rate may be reduced.

US 2012/195486 A1 discloses a remote photoplethysmographic system for remotely determining the heart rate of a living being. The system comprises several light sources for irradiating the living being and a video camera for remotely capturing a video image of the living being. The system is adapted to determine the heart rate based on the remotely captured video image.

SUMMARY OF THE INVENTION

It is an object of the present invention to provide a physiological property determination apparatus, method and computer program, which allow for an improved determination of a physiological property of a person.

In a first aspect of the present invention a physiological property determination apparatus for determining a physiological property of a person is presented, wherein the physiological property determination apparatus comprises:
- at least two light sources for emitting at least two light beams having different wavelengths into tissue of the person,
- a light detector having a two-dimensional detection surface for detecting light, which has travelled through the tissue, wavelength-dependently and for generating a wavelength-dependent two-dimensional image based on the detected light,
- a controller for separately controlling the intensities of the light beams of the different light sources such that the light detector is not overloaded, and
- a physiological property determination unit for determining the physiological property based on the generated wavelength-dependent two-dimensional image.

Since the controller is adapted to separately control the intensities of the light beams of the different light sources, for each wavelength the illumination of the tissue of the person can be independently optimized, for instance such that the signal-to-noise ratio is optimized for each respective wavelength. This can lead to an improved determination of the physiological property based on the wavelength-dependent two-dimensional image. The physiological property determination unit is for example adapted to determine the pulse rate as the physiological property. The controller being adapted to separately control the intensities of the light beams such that the light detector is not overloaded, this leads to a further improved quality of determining the physiological property.

In an embodiment the at least two light sources include three light sources emitting three different light beams having different wavelengths. The light sources are for example adapted to emit blue, green and red light beams. The light sources preferably include a laser and/or a light-emitting diode (LED). The two-dimensional detection surface preferably comprises a two-dimensional arrangement of detection elements, each detection element generating wavelength-dependent detection signals for generating the wavelength-dependent two-dimensional image. The wavelength-dependent two-dimensional image is for example temporally dependent and comprises several two-dimensional image frames for different times.

In an embodiment the apparatus further comprises a spacer being transparent for the light beams, wherein the spacer is arranged in front of the detection surface. The spacer is for example used, if the light sources are lasers emitting coherent light, wherein in this case, when using the spacer, a speckle image is generated by the light detector, which can be used by the physiological property determination unit for determining the physiological property.

In another embodiment the controller may be adapted to control the light sources such that the detection surface does not receive the maximal amount of light, which would be possible without overloading the light detector, but a smaller amount of light. The difference between the maximal amount and the smaller amount may be predetermined or determined for the different wavelengths by the controller. It may correspond to an expected fluctuation of the detected light intensity due to motion of the physiological property determination apparatus. For instance, the controller can be adapted to distinguish light intensity fluctuations caused by the physiological property to be measured from other kinds of light intensity fluctuations, which may be caused by motion, and to control the light sources such that the light detector is not overloaded, even if the other kinds of light fluctuations are present. If the physiological property is known to cause light intensity fluctuations within a certain frequency range, light intensity fluctuations outside this frequency range can be observed and a corresponding maximal amplitude of the fluctuating intensity can be determined. The difference between the maximal amount of light and the smaller amount of light may correspond to this maximal amplitude. After the difference has been determined, it may be stored in the controller and used for further measurements. Controlling the light intensities of the light beams emitted by the light sources to this smaller amount of light can ensure that the light detector does not overload, even if the detected light intensity fluctuates due to, for instance, motion.

The difference may also be determined in another way. For instance, the physiological property determination unit can further comprise a motion sensor for generating a motion signal being indicative of the motion of the physiological property determination apparatus, wherein this motion signal can be used by the controller to distinguish the light intensity fluctuations caused by the physiological property to be measured from light intensity fluctuations caused by the motion. In particular, the motion signal can define a frequency range in which the detected light intensity fluctuates due to motion, wherein the maximal detected light intensity fluctuation amplitude within this frequency range can be used as the difference between the maximal amount and the smaller amount. The controller can also be adapted to use other techniques for determining motion-induced light intensity fluctuations by correlating the detected light intensity with the motion signal.

The two-dimensional detection surface preferably comprises a two-dimensional arrangement of detection elements, each detection element generating wavelength-dependent detection signals for generating the wavelength-dependent two-dimensional image, wherein the physiological property determination unit is adapted to determine the physiological property a) by individually processing the detection signals generated by different detection elements or b) by determining for different groups of detection elements group detection signals based on the detection signals generated by the respective group of detection elements and by individually processing the group detection signals. For instance, the detection signals of a group of detection elements can be averaged for determining a group detection signal. In particular, the physiological property determination unit is adapted to determine a degree of disturbance of the respective detection signal or group detection signal by motion and to determine the physiological property based on detection signals or group detection signals having a degree of disturbance being smaller than a disturbance threshold. For instance, the physiological property determination apparatus may further comprise a motion sensor for generating a motion signal being indicative of a motion of the physiological property determination apparatus, wherein the physiological property determination unit may be adapted to determine the degree of disturbance of the respective detection signal or group detection signal based on the motion signal. Thus, detection signals or group detection signals are determined for different wavelengths, i.e. colors, and for different locations on the tissue, wherein the disturbance of detection signals or group detection signals may be different for different colors and/or for different locations of the respective detection element or group of detection elements. Among these detection signals only the detection signals may be selected, which are only little disturbed or not disturbed at all by motion. For instance, the selected detection signals can be combined, especially averaged, and the number of pulses of the combined selected detection signal per minute can be determined as the pulse rate. Using the selected detection signals for determining the physiological property can further improve this determination.

In an embodiment the physiological property determination unit is adapted to determine the physiological property by linearly combining the detection signals. In particular, the physiological property determination unit is adapted to linearly combine the detection signals or group detection signals such that movement artifacts in the linearly combined detection signals are smaller than in the detection signals before being linearly combined. For instance, the physiological property determination unit may be adapted to apply a principal component analysis (PCA) to the detection signals for linearly combining the detection signals. The physiological property determination unit may then be adapted to determine the physiological property based on the linearly combined signals, especially on the principal component obtained from the PCA. Thus, the linear combination may "clean" the signals from movement artifacts, thereby further improving the determination of the physiological property.

The several light sources and the light detector are for example adapted to generate the wavelength-dependent two-dimensional image such that it is temporally dependent and comprises several two-dimensional image frames for different times, wherein the physiological property determination unit can be adapted to determine corresponding regions in different image frames and to determine the physiological property based on these corresponding regions in the different image frames. For instance, detection signals in a region in a certain image frame can be combined, for example, linearly combined as described above, especially averaged, in order to determine for the certain image frame a combined signal. By determining this combined signal for different image frames, a time-dependent signal can be generated, which can be used by the physiological property determination unit for determining the physiological property. For example, the repetition rate of the signal can be determined as a pulse rate. For determining the corresponding regions in the different image frames known image registration techniques may be used, or other known techniques for finding corresponding elements and, thus, regions in different images, which may be correlation based.

The controller may be adapted to control the light sources such that the intensities of the light beams are varied. For instance, the light sources may be operable in a pulsed mode in which the light beams are emitted as light pulses into the tissue. Operating the light sources in a pulsed mode is less power consuming than operating the light sources in a continuous mode. Thus, by operating the light sources in the pulsed mode the power consumption of the physiological property determination apparatus can be reduced. Moreover, the controller may be adapted to control the light sources such that each light source repeatedly emits at least two light pulses having different intensities. If the light intensity is relatively small, at locations on the two-dimensional detection surface having a relatively large distance to the respective light source the intensity of the detected light may be relatively small or the light may not even be measurable because of the relatively long travel distance within the tissue, whereas at locations on the two-dimensional detection surface having a relatively small distance to the respective light source the light may be well detectable without overloading the detection elements at this location. If the light intensity is relatively large, at locations on the two-dimensional detection surface having a relatively large distance to the respective light source the light may be well detectable, whereas at locations on the two-dimensional detection surface having a relatively small distance to the respective light source the detection elements may be overload. Thus, by combining light detection measurements, which have been performed while the light sources emitted light having different intensities, it can be ensured that the light is well detectable at different locations on the two-dimensional detection surface.

The physiological property determination apparatus comprises for example an attaching element for attaching at least the light sources and the light detector to the wrist of the person. Thus, the physiological property determination apparatus can be a watch-like device to be worn on the wrist of the person.

In a further aspect of the present invention a physiological property determination method for determining a physiological property of a person is presented, wherein the physiological property determination method comprises:

emitting at least two light beams having different wavelengths into tissue of the person by at least two light sources, detecting light, which has travelled through the tissue, wavelength-dependently and generating a wavelength-dependent two-dimensional image based on the detected light by a light detector having a two-dimensional detection surface, separately controlling the intensities of the light beams of the different light sources by a controller such that the light detector is not overloaded, and determining the physiological property based on the generated wavelength-dependent two-dimensional image by a physiological property determination unit.

In another aspect of the present invention a computer program for determining a physiological property of a person is presented, wherein the computer program comprises program code means for causing a physiological property determination apparatus as defined in claim 1 to carry out the steps of the physiological property determination method as defined in claim 14, when the computer program is run on a computer controlling the physiological property determination apparatus.

It shall be understood that the physiological property determination apparatus of claim 1, the physiological property determination method of claim 13 and the computer program of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The invention relates to a physiological property determination apparatus for determining a physiological property like a pulse rate of a person, wherein the apparatus may be configured to be worn on the wrist like a watch. A controller separately controls several light sources for emitting several light beams having different wavelengths into tissue of the person and a light detector having a two-dimensional detection surface detects light, which has travelled through the tissue, wavelength-dependently and generates a wavelength-dependent two-dimensional image based on the detected light. Based on the generated wavelength-dependent two-dimensional image the physiological property is determined. The separate control of the light sources allows for an independent optimization of the illumination and detection processes for each wavelength, which in turn can lead to an improved determination of the physiological property based on the wavelength-dependent two-dimensional image.

Figure 1:
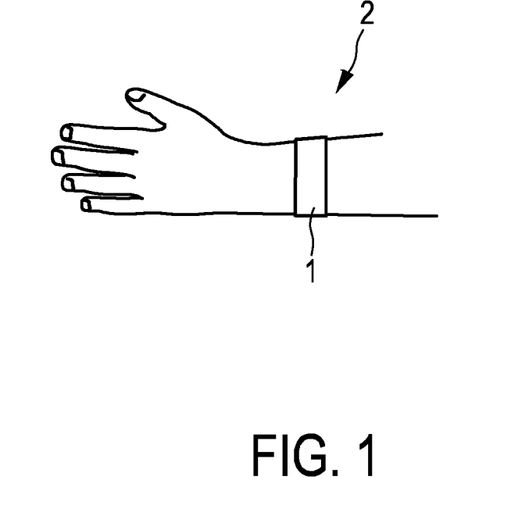
FIG. 1 shows schematically and exemplarily an embodiment of a physiological property determination apparatus for determining a physiological property of a person to be worn on a wrist of a person.

FIG. 1 shows schematically and exemplarily an embodiment of a physiological property determination apparatus for determining a physiological property of a person. In this embodiment the physiological property determination apparatus 1 is adapted to be worn on the wrist 2 of the person. Moreover, the physiological property determination apparatus is adapted to determine the pulse rate of the person as the physiological property. The physiological property determination apparatus 1 is schematically and exemplarily shown in more detail in FIG. 2.

Figure 2:
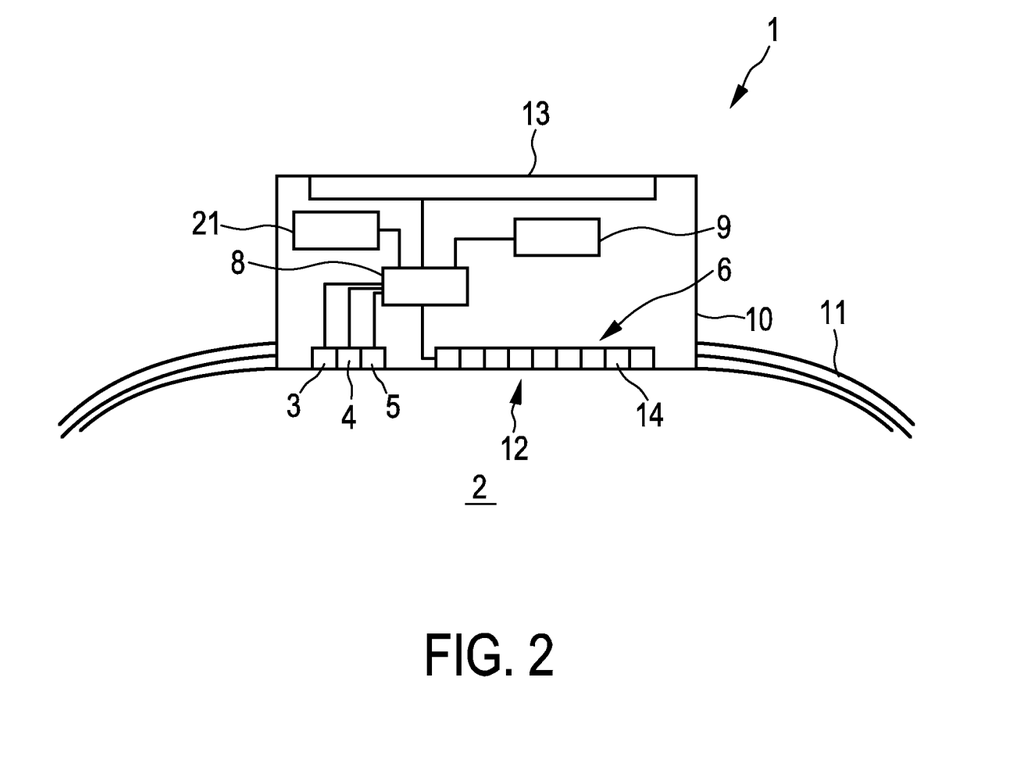
FIG. 2 shows schematically and exemplarily the embodiment of the physiological property determination apparatus in more detail.

The physiological property determination apparatus 1 comprises three light sources 3, 4, 5 for emitting light beams having different wavelengths into the person at the wrist 2. The light beams travel through a part of the wrist 2, in particular, through tissue of the person at the wrist 2, wherein the light beams are backscattered by, for instance, the tissue and blood. The backscattered light is detected by a light detector 6 having a two-dimensional detection surface 12 wavelength-dependently. The two-dimensional detection surface 12 comprises a two-dimensional arrangement of detection elements 14, wherein each detection element 14 generates wavelength-dependent detection signals for generating the wavelength-dependent two-dimensional image. The light detector 6 is, for instance, a charge-coupled device (CCD) detector or a complementary metal-oxide semiconductor (CMOS) detector. It is adapted to generate three two-dimensional images for the three colors, wherein each image is a temporal image, i.e. they comprise several image frames for different time instants, in order to indicate temporal changes of the detection signals which are used by a physiological property determination unit 9 for determining the physiological property.

The light sources 3, 4, 5 are for example LEDs. However, they can also be other kinds of light sources like lasers. In this embodiment the three light sources 3, 4, 5 are adapted to emit a blue light beam, a green light beam and a red light beam, respectively, wherein each detection element is adapted to generate separate detection signals for the blue, green and red light beams, respectively. Thus, the light detector 6 comprises three color channels, wherein for each color channel a two-dimensional image is generated based on the detection signals generated for the respective colors.

The physiological property determination apparatus 1 further comprises a controller 8 for separately controlling the intensities of the light beams of the different light sources 3, 4, 5. The controller 8 is for example adapted to separately control the intensities of the light beams of the different light sources 3, 4, 5 such that the light detector 6 is not overloaded. In particular, the light detector 6 is adapted to provide an overload signal to the controller 8, if a color channel of a detection element 14 is overloaded, wherein, if the controller 8 receives such an overload signal, the controller 8 reduces the light intensity of the respective color such that the overload situation is not present anymore. Thus, the light sources 3, 4, 5 can be controlled such that for each color the detection surface 12 receives a maximal amount of light, without overloading any detection element 14 of the detection surface 12.

Since the detection signals may fluctuate due to motion, the controller 8 may be adapted to control the light sources 3, 4, 5 such that the detection surface 12 does not receive the maximal amount of light, which would be possible without overloading the light detector if possible movements and hence corresponding fluctuations in the detection signals are not considered, but a smaller amount of light. The difference between the maximal amount and the smaller amount may be predetermined or determined for different colors by the controller 8. It may correspond to an expected maximal motion-induced fluctuation amplitude of the detected light intensity. For instance, the controller 8 can be adapted to distinguish signal fluctuations caused by the physiological property to be measured from the motion-induced signal fluctuations and to control the light sources 3, 4, 5 such that the light detector 6 is not overloaded, even if the motion-induced signal fluctuations are present. In order to determine an expected maximal motion-induced fluctuation amplitude, the two-dimensional image, i.e. the detection signals forming the image, may be frequency filtered. For instance, if the physiological property is known to cause detection signal fluctuations within a certain frequency range, detection signal fluctuations outside this frequency range can be observed and a corresponding maximal amplitude of the fluctuating detection signal can be determined. The difference between the maximal amount of light and the smaller amount of light may correspond to this maximal amplitude. After this difference has been determined, it may be stored in the controller 8 and used for further measurements. Controlling the light intensities of the light beams emitted by the light sources 3, 4, 5 to the smaller amount of light can ensure that the light detector 6 does not overload, even if the detected light intensities fluctuate due to motion.

The difference may also be determined in another way. For instance, the physiological property determination unit can further comprise a motion sensor 21 like an accelerometer for generating a motion signal being indicative of the motion of the physiological property determination apparatus 1, wherein this motion signal can be used by the controller 8 to distinguish the signal fluctuations caused by the physiological property to be measured from the motion-induced signal fluctuations. In particular, the motion signal can define a frequency range in which the detected light intensity fluctuates due to motion, wherein the maximal amplitude of the signal fluctuations within this frequency range can define the difference between the maximal and smaller amount. The controller 8 can also be adapted to use other correlation based techniques, in order to determine motion-induced detection signal fluctuations by correlating the light detection signal with the motion signal. For example, a repetitive rate of the motion signal can be determined, wherein an amplitude of a detection signal fluctuating with this repetitive rate may be used for determining the difference between the maximal amount of light and smaller amount of light.

Normally, blood vessels that are deeper within the skin have a larger diameter and the blood within these blood vessels has a larger blood pressure. Red light penetrates relatively deeply into the skin and leads therefore to a relatively pronounced pulse contribution in the red color channel. However, the corresponding detection signal may be also influenced by mechanical motion of the physiological property determination apparatus 1. The green light penetrates not as deep as the red light, but deeper than the blue light that penetrates substantially only the first layers of the skin. The green light still leads to a detection signal in which the pulse contribution may be well detectable, wherein in comparison to the red detection signal mechanical motion artifacts are less pronounced. In the blue detection signal the pulse contribution is the weakest, but also the influence by mechanical motion artifacts, which may be caused by motion of the physiological property determination apparatus, is relatively small. Moreover, the blue light detection signal may be influenced by a sloshing movement artifact which may be caused by the blood movement. The physiological property determination unit 9 is for example adapted to use the detection signals, which are generated by using red, green and blue light and which therefore show different characteristics, for determining the pulse rate.

In particular, the physiological property determination unit 9 is adapted to determine the pulse rate by individually processing the detection signals generated by the detection elements 14 of the two-dimensional detection surface 12 for the blue, green and red colors. The physiological property determination unit may also be adapted to determine the physiological property by determining for different groups of detection elements group detection signals based on the detection signals generated by the respective group of detection elements and by individually processing the group detection signals. For instance, the detection signals of a group of detection elements can be averaged for determining a group detection signal.

The physiological property determination unit 9 can be adapted to determine a degree of disturbance of the respective detection signal by motion and to determine the physiological property based on detection signals having a degree of disturbance being smaller than a disturbance threshold. For instance, the physiological property determination unit 9 may be adapted to determine the degree of disturbance of the respective detection signal based on the motion signal generated by the motion sensor 21. In particular, if the repetitive rate in the motion signal is similar to a repetitive rate in a light detection signal, it can be assumed that the light detection signal is strongly disturbed, whereas, if the repetitive rate of the motion signal is not or only weakly observable in a light detection signal, it may be assumed that there is no disturbance or a weak disturbance only. For determining the degree of disturbance a correlation may be calculated for the motion signal and the respective light detection signal.

Detection signals are determined for different wavelengths, i.e. colors, and for different locations on the tissue, wherein the disturbance of the detection signals may be different for different colors and/or for different locations of the respective detection element. Among these detection signals only the detection signals may be selected, which are only little disturbed or not disturbed at all by motion. Using these selected detection signals for determining the physiological property can further improve this determination. For instance, the selected detection signals can be combined, especially averaged, and the number of pulses of the combined selected detection signal per minute can be determined as the pulse rate.

In an embodiment the physiological property determination unit 9 is adapted to determine the physiological property by linearly combining the detection signals. In particular, the physiological property determination unit can be adapted to linearly combine the detection signals such that movement artifacts in the linearly combined detection signals are smaller than in the detection signals before being linearly combined. For instance, the physiological property determination unit 9 may be adapted to apply a PCA to the detection signals for linearly combining the detection signals. The physiological property determination unit 9 may then be adapted to determine the physiological property based on the linearly combined signals, especially on the principal component obtained from the PCA. Thus, the linear combination may "clean" the signals from movement artifacts, wherein the physiological property determination unit 9 may be adapted to determine a repetitive rate of the cleaned detection signals as the pulse rate.

Before linearly combining the different light detection signals, the light detection signals may be weighted, wherein light detection signals, which correspond to tissue regions where the perfusion is larger, may obtain a larger weight than the light detection signals, which correspond to tissue regions where the perfusion is smaller. For example, amplitudes of the light detection signals while the physiological property determination apparatus is in rest, i.e. does not move, are used as values being indicative of the respective amount of perfusion. That means, for instance, in an embodiment amplitudes of the light detection signals are determined for each detection element and for each wavelength, while the physiological property determination apparatus does not move, wherein then for each combination of a detection element and a wavelength a weight is determined depending on the respective amplitude. These weights can be stored and used for determining the physiological property, especially the pulse rate.

The physiological property determination unit 9 may also be adapted to determine corresponding regions in different image frames and to determine the physiological property based on these corresponding regions in the different image frames. For instance, detection signals generated by detection elements 14 within a region in a certain image frame can be combined, for instance, linearly combined as described above or averaged, in order to determine for the certain image frame a combined signal. By determining this combined signal for different image frames, a time-dependent signal can be generated, which can be used by the physiological property determination unit 9 for determining the physiological property. For example, a repetition rate of the time-dependent signal can be determined as a pulse rate. For determining the corresponding regions in the different image frames known image registration techniques or other known techniques for finding corresponding elements and hence regions in different images, which may be correlation based, may be used.

The light sources 3, 4, 5 may be controlled to be operated in a continuous mode. However, the controller 8 is also adapted to control the light sources 3, 4, 5 such that the intensities of the light beams are varied. In particular, the light sources 3, 4, 5 are operated in a pulsed mode in which the light beams are emitted as light pulses into the tissue. The controller 8 is also adapted to control the light sources 3, 4, 5 such that each light source 3, 4, 5 repeatedly emits at least two light pulses having different intensities. If the light intensity is relatively small, at locations on the two-dimensional detection surface 12 having a relatively large distance to the respective light source 3, 4, 5 the intensity of the detected light may be relatively small or the light may not even be measurable because of the relatively long travel distance within the tissue, whereas at locations on the two-dimensional detection surface 12 having a relatively small distance to the respective light source 3, 4, 5 the light may be well detectable without overloading the detection elements 14 at this location. If the light intensity is relatively large, at locations on the two-dimensional detection surface 12 having a relatively large distance to the respective light source 3, 4, 5 the light may be well detectable, whereas at locations on the two-dimensional detection surface 12 having a relatively small distance to the respective light source 3, 4, 5 the detection elements 14 may be overload. The physiological property determination unit 9 is for example adapted to not use overloaded light detection signals and too small light detection signals, i.e. light detection signals being smaller than a predefined threshold which may be determined by calibration, for determining the pulse rate. That means, from the light detection signals generated while the emitted light intensities were relatively small preferably only light detection signals are used, which were generated by detection elements 14 being relative close to the light sources 3, 4, 5, whereas from the light detection signals generated while the emitted light intensities were relatively large preferably only light detection signals are used, which were generated by detection elements 14 having a larger distance to the light sources 3, 4, 5. The physiological property determination apparatus 1 further comprises an attaching element 11 for attaching at least the light sources 3, 4, 5 and the light detector 6 to the wrist 2 of the person such that they are directly located on the skin of the wrist 2. In this embodiment the attaching element 11 is a wristband such that the physiological property determination apparatus 1 is a watch-like device adapted to be worn on the wrist 2 of the person.

The physiological property determination apparatus 1 may further comprise a display 13 for displaying the determined physiological property. Moreover, the different components of the physiological property determination apparatus 1 may be in enclosed in a casing 10.

Figure 3:
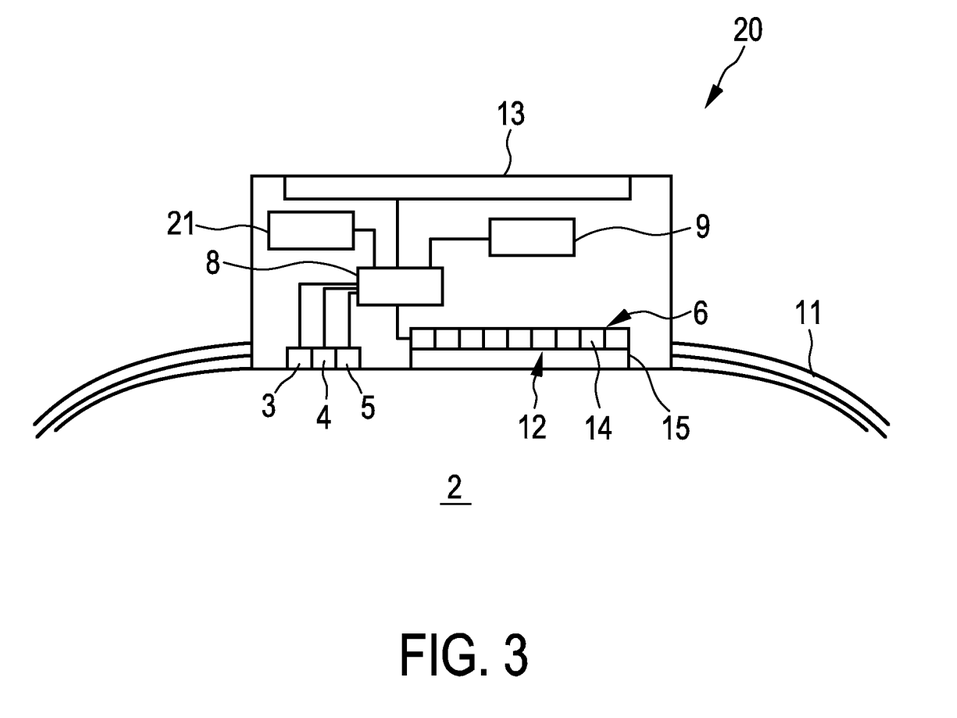
FIG. 3 shows schematically and exemplarily a further embodiment of a physiological property determination apparatus.

FIG. 3 shows schematically and exemplarily a further embodiment of the physiological property determination apparatus. The physiological property determination apparatus 20 schematically and exemplarily shown in FIG. 3 is similar to the physiological property determination apparatus 1 schematically and exemplarily shown in FIG. 2, except for an additional transparent spacer 15, which is arranged between the two-dimensional detection surface 12 and the wrist 2. The spacer 15 has for example a thickness being equal to or larger than 5 mm. Moreover, in the embodiment exemplarily and schematically shown in FIG. 3 the three light sources 4, 5, 6 are for example lasers emitting coherent light, in order to allow the light detector 6 to generate two-dimensional speckle images. The spacer 15 is transparent for the wavelengths of the light beams emitted by the light sources 3, 4, 5. It may be a transparent glass plate. However, the spacer may also be made of a scattering material, in order to increase the speckle contrast.

Also in this embodiment the physiological property determination apparatus is for example adapted to determine the pulse rate of the person as the physiological property. In particular, in this embodiment the physiological property determination unit 9 is for example adapted to determine corresponding regions in different image frames and to determine the physiological property based on these corresponding regions in the different image frames. For instance, detection signals generated by detection elements 14 within a region in a certain image frame can be combined, for instance, linearly combined as described above or averaged, in order to determine for the certain image frame a combined signal. By determining this combined signal for different image frames, a time-dependent signal can be generated, which can be used by the physiological property determination unit 9 for determining the physiological property. It is also possible to determine the contrast in the corresponding regions in the different image frames, wherein in this case the contrast determined for the different image frames forms a temporal signal which can be used for determining the pulse rate.

Figure 4:
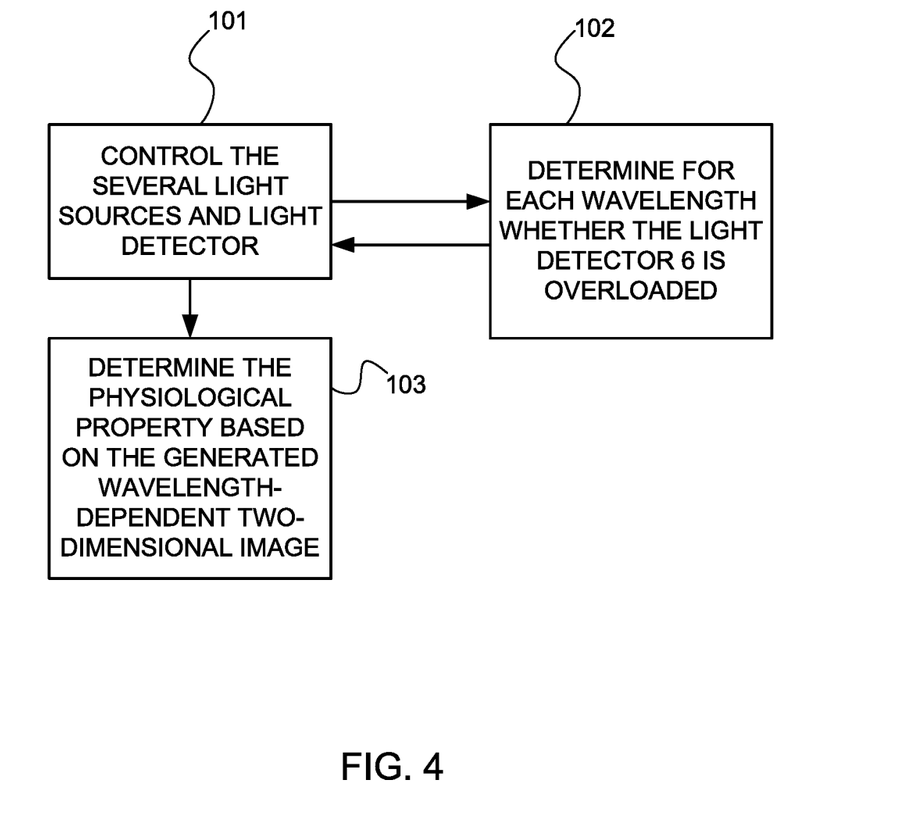
FIG. 4 shows a flowchart exemplarily illustrating an embodiment of a physiological property determination method for determining a physiological property of a person.

In the following an embodiment of a physiological property determination method for determining a physiological property of a person will exemplarily be described with reference to a flowchart shown in FIG. 4.

In step 101 the controller 8 controls the several light sources 3, 4, 5 such that they emit several light beams having different wavelengths into the person at the wrist 2. Moreover, the controller 8 controls the light detector 6 to detect the light, after it has travelled through the wrist 2 of the person, wavelength-dependently and to generate a wavelength-dependent two-dimensional image, i.e., for instance, three two-dimensional images for blue, green and red colors, based on the detected light. In step 102, concurrently with step 101, it is determined for each wavelength whether the light detector 6 is overloaded. This overload information is then used by the controller 8 to control the light sources 3, 4, 5 such that the intensities of the light beams are maximized, without overloading the light detector 6 at any wavelength. In step 103 the physiological property determination unit 9 determines the physiological property based on the generated wavelength-dependent two-dimensional image, i.e., for example, based on the three two-dimensional images generated for the blue, green and red colors. Steps 101 to 103 can be performed in a loop such that repeatedly, for instance, in a pulsed way or continuously, the several light beams are emitted into the tissue of the person and, after having travelled through the tissue, detected, wherein the light intensities may be maximized without overloading the detector and wherein the physiological property determination unit may repeatedly determine the physiological property based on the repeatedly detected light, i.e. based on the repeatedly generated wavelength-dependent two-dimensional image.

The light detector can be regarded as being a camera, which is brought into contact with the tissue at the wrist of the person, in order to measure the pulse rate, i.e. the heart rate, on the wrist. The light detector detects the light, which has been scattered in the skin and which may have been absorbed more or less by the blood. The detection signals generated by the detection elements of the two-dimensional detection surface depend on the blood volume having absorbed the light. When the heart pulsates, the blood volume in the skin changes and thus the detection signals generated by the detection elements of the two-dimensional detection surface change as well. The physiological property determination apparatus as described above with reference to FIGS. 1 to 3 allows for a reliable determination of the pulse rate based on the variations in the detection signals generated by the different detection elements of the two-dimensional detection surface, even if the wrist of the person is moved.

A detection signal generated by a detection element, i.e. by a pixel of the two-dimensional detection surface, depends on the distance of the detection element to the respective light source. If the distance is larger, the detection signal will generally indicate a smaller detected intensity, and if the distance is smaller, the detection signal will generally indicate a larger detected intensity. Thus, because of the different distances between a) the detection elements and b) the light sources, the two-dimensional image will show intensity variations depending on the distances. These intensity variations occur, because the light detected by a detection element having a larger distance to the light sources has travelled through a deeper and larger part of the tissue than the light detected by a detection element being closer to the light sources. The detection signals, which are generated based on light having travelled through a deeper and larger part of the tissue, are supposed to have a relatively large pulse component, because this light was stronger influenced by the blood.

Since the different distances between the detection elements and the light sources and also the different wavelengths lead to different penetration depths of the detected light, the two-dimensional image provides depth-resolution information. This penetration depth information is used by the physiological property determination apparatus described above with reference to FIGS. 1 to 3 for reliably determining the physiological property, even if the person's wrist, in particular, the person's hand, is moved.

The light detector may be adapted to generate a respective first image, when the light sources do not emit light, and a respective second image, when the light sources emit light, wherein the first and second images can be subtracted from each other and wherein the respective resulting subtraction image can be used for further processing. Using such subtraction images, which may be generated for different time instants, for processing can result to a reduction of ambient artifacts generated by ambient light, which may be present. Moreover, the physiological property determination apparatus can comprises a signal-to-noise ratio determination unit for determining wavelength-dependent signal-to-noise ratios for the wavelength-dependent light detection. Thus, for instance, for each of the three colors a signal-to-noise ratio may be determined for the respective two-dimensional image, wherein the controller can be adapted to separately control the different light sources depending on the respective determined signal-to-noise ratios, especially such that the signal-to-noise ratio is separately optimized for each wavelength without overloading the light detector. The signal-to-noise ratio can depend on electronic noise and/or movements of the physiological property determination apparatus.

The physiological property determination apparatus has for example three light sources optimized for performance and power consumption, wherein the three light sources are for example adapted to emit blue, green and red light. By changing the power of each of the three light sources, i.e. by changing the intensity of the respective light beams, the signal-to-noise ratio in each color channel of the light detector may be optimized, without overloading the light detector. If the light sources are lasers, preferably an optically transparent spacer is arranged between the light detector and the skin of the person. The physiological property determination apparatus is for example adapted to take advantage of differences between distances of different detection elements, i.e. pixels, to the three light sources, wherein the detection signals generated by the different detection elements are for example individually processed for determining the physiological property.

Although in above described embodiments three light sources have been used for generating three different light beams having different wavelengths, i.e. different colors, in other embodiments two or more than three light sources may be used for generating two or more than three light beams having different colors. Moreover, although in above described embodiments the three light sources emit blue, green and red light beams, in other embodiments the light sources can emit light beams having other colors.

Although in above described embodiments the physiological property determination apparatus is adapted to determine the pulse rate as a physiological property, in other embodiments the physiological property determination apparatus can be adapted to determine another physiological property based on the two-dimensional images like the oxygenation of blood, wherein, if the physiological property determination apparatus is adapted to determine the oxygenation of blood, at least two light sources emitting red and green light are for example used.

Although in above described embodiments the physiological property determination apparatus is adapted to be worn on the wrist of the person, in order to determine the physiological property at the wrist, in other embodiments the physiological property determination apparatus can be adapted to determine the physiological property at another part of the person like a finger, an arm, a leg, the breast, et cetera.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of two or more items recited in the claims. The mere fact that certain measures are recited in mutually different dependent claims does not indicate that a combination of these measures cannot be used to advantage.

Procedures like the determination of a physiological property, the control of the light sources, et cetera performed by one or more units or devices can be performed by any other number of units or devices. These procedures and the control of the physiological property determination apparatus in accordance with the physiological property determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A physiological property determination apparatus for determining a physiological property of a person, the physiological property determination apparatus comprising:
   at least two light sources that emit at least two light beams having different wavelengths into tissue of the person;
   a light detector comprising a two-dimensional light detection surface,
      wherein the two-dimensional detection surface comprises a two-dimensional arrangement of light detection elements,
         wherein each detection element generates wavelength-dependent detection signals corresponding to detected light from the tissue, and
         wherein the two dimensional arrangement of light detectors provide a wavelength-dependent two-dimensional image;
   a processor that separately controls an intensity of each of the at least two light sources,
      wherein the light detector provides one or more overload signals to the processor if one or more of the light detection elements are overloaded, and
      wherein the processor controls the intensity of each of the at least two light sources based on the one or more overload signals to avoid overloading the light detection elements,
   a physiological property determination circuit that determines the physiological property based on the wavelength-dependent two-dimensional image,
      wherein the physiological property determination circuit determines the physiological property by:
         weighting the detection signals to provide weighted detection signals based on perfusion of regions of the tissue,
            wherein a larger weight is assigned to regions having higher perfusion, and a smaller weight is assigned to regions having a lower perfusion, and
         linearly combining the weighted detection signals.

2. The physiological property determination apparatus of claim 1, wherein the at least two light sources include three light sources emitting three different light beams having different wavelengths.

3. The physiological property determination apparatus of claim 2, wherein the light sources are adapted to emit blue, green and red light beams.

4. The physiological property determination apparatus of claim 1, wherein the apparatus further comprises a spacer being transparent for the light beams, wherein the spacer is arranged in front of the detection surface.

5. The physiological property determination apparatus of claim 1, wherein the physiological property determination circuit is adapted to determine the physiological property a) by individually processing the detection signal generated by different detection elements or b) by determining for different groups of detection elements group detection signals based on the detection signals generated by the respective group of detection elements and by individually processing the group detection signals.

6. The physiological property determination apparatus of claim 5, wherein the physiological property determination circuit is adapted to determine a degree of disturbance of the respective detection signal or group detection signal by motion and to determine the physiological property based on detection signals or group detection signals having a degree of disturbance being smaller than a disturbance threshold.

7. The physiological property determination apparatus of claim 6, wherein the physiological property determination apparatus further comprises a motion sensor for generating a motion signal being indicative of a motion of the physiological property determination apparatus and wherein the physiological property determination circuit is adapted to determine the degree of disturbance of the respective detection signal or group detection signal based on the motion signal.

8. The physiological property determination apparatus of claim 1, wherein the processor circuit is adapted to control the light sources such that the intensities of the light beams are varied.

9. The physiological property determination apparatus of claim 1, wherein the physiological property determination apparatus further comprises an attaching element for attaching at least the light sources and the light detector to a wrist of the person.

10. The physiological property determination apparatus of claim 1, wherein the physiological property determination circuit is adapted to determine a pulse rate as the physiological property.

11. The physiological property determination apparatus of claim 1,
   wherein the at least two light sources and the light detector generate the wavelength-dependent two-dimensional image such that it is temporally dependent and comprises at least two two-dimensional image frames for different times, and wherein the physiological property determination circuit determines corresponding regions in different image frames and determines the physiological property based on these corresponding regions in the different image frames.

12. A physiological property determination apparatus for determining a physiological property of a person, the physiological property determination apparatus comprising:
- at least two light sources for emitting at least two light beams having different wavelengths into tissue of the person,
- a light detector having a two-dimensional detection surface for detecting the at least two light beams after they have travelled through the tissue, wavelength-dependently and for generating a wavelength-dependent two-dimensional image based on the detected light, wherein the two-dimensional detection surface comprises a two-dimensional arrangement of detection elements, each of the detection elements generating wavelength-dependent detection signals for generating the wavelength-dependent two-dimensional image,
- a motion sensor for generating a motion signal being indicative of a motion of the physiological property determination apparatus,
- a processor circuit for separately controlling the intensities of the at least two light beams of the at least two light sources based on the motion signal such that the light detector is not overloaded, and
- a physiological property determination circuit for determining the physiological property based on the generated wavelength-dependent two-dimensional image, wherein the determining of the physiological property includes linearly combining the detection signals.

13. The physiological property determination apparatus of claim 12, wherein the physiological property determination circuit is adapted to determine a degree of disturbance of the respective wavelength-dependent detection signals by motion and to determine the physiological property based on a subset of the wavelength-dependent detection signals having a degree of disturbance being smaller than a disturbance threshold.

14. The physiological property determination apparatus of claim 13, wherein the physiological property determination circuit is adapted to determine the degree of disturbance of the respective wavelength-dependent detection signals based on the motion signal.

15. A method comprising:
- emitting at least two light beams having different wavelengths into tissue of a person;
- detecting wavelength-dependent signals from a light detector comprising a two-dimensional detection surface,
  - wherein the two-dimensional detection surface comprises a two-dimensional arrangement of light detection elements,
    - wherein each detection element generates wavelength-dependent detection signals corresponding to detected light from the tissue, and
    - wherein the two dimensional arrangement of light detectors provide a wavelength-dependent two-dimensional image;
- providing one or more overload signals from the light detector if one or more of the light detection elements are overloaded;
- separately controlling an intensity of each of the at least two light sources based on the one or more overload signals to avoid overloading the light detection elements,
- determining the physiological property based on the wavelength-dependent two-dimensional image by:
  - weighting the detection signals to provide weighted detection signals based on perfusion of regions of the tissue,
  - wherein a larger weight is assigned to regions having higher perfusion, and a smaller weight is assigned to regions having a lower perfusion, and
- linearly combining the weighted detection signals.

* * * * *